June 13, 1961 C. H. FISCHER Plant Pat. 2,062
GLADIOLUS PLANT
Filed Aug. 23, 1960
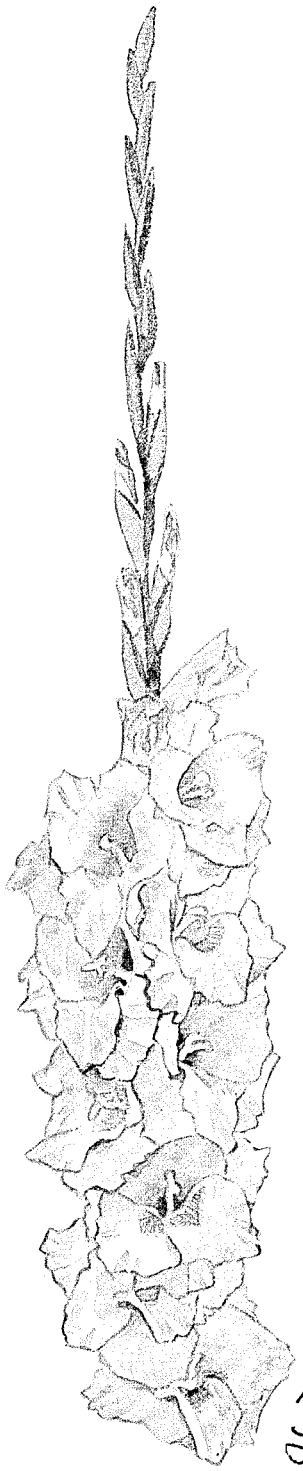
INVENTOR
CARL H. FISCHER
ATTORNEY
Lamont Johnston United States Patent Office Plant Pat. 2,062
Patented June 13, 1961

2,062
GLADIOLUS PLANT

Carl H. Fischer, St. Charles, Minn., assignor to Selected Glads, Inc., New Albany, Ind., a corporation of Tennessee Filed Aug. 23, 1960, Ser. No. 51,476
1 Claim. (Cl. 47—60)

My present invention relates to a new and improved variety of gladiolus plant and is notable particularly for its color, size and consistency of performance.

To the best of my knowledge, this new variety is the result of a cross between the varieties Libretto (unpatented) and Caribbean (Plant Patent No. 1654), Libretto being the seed parent and Caribbean the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this variety, reduced in size, and is as nearly true to color as it is possible to depict. The illustration shows how the petals lie together nicely in double-row placement. It shows the ruffling and deeper blotch, also.

In the following detailed description, color plate references are to the "Horticultural Colour Chart," by The British Colour Council. Where there are other references to color, the ordinary dictionary meanings of the terms are intended.

*The plant*

Growth: Extremely vigorous, averaging 55 to 60 inches in height. Propagates easily.

Blooming: Each spike opens from eight to ten 5½ to 5¾ inch flowers at one time. Successive blooms open, totalling an average of twenty to twenty-four florets to each spike. The variety is a mid-season bloomer, blooming on the average in 80 days from large bulbs.

Stems: Straight and strong; diameter at base is ½ to ¾ inch.

Foliage: Healthy green; average leaf is 1½ to 2 inches wide and the plant is 24 to 30 inches high.

Disease resistance: This variety is very resistant to disease. It has been found resistant to Sclerotina Dry Rot, Septoria Leaf Spot and Fusarium Yellows to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases, whereas this variety remained healthy and unaffected.

Corms: Heavy, well-husked and plump; average 2 to 2½ inches in diameter from adult plants.

*The flower*

Spike: Tall, has twenty to twenty-four buds of which four to five open the first day, following which eight to ten are open until all have opened.

Bud:

*Size.*—Opening buds are 2½ to 2¾ inches long.

*Opening.*—Five to seven will show color at one time.

Flower:

*Arrangement.*—Flowers are formally placed in a double row on the stem and usually all face forward.

*Size.*—Individual florets are large, usually measuring 5½ to 5¾ inches in diameter. Upper blooms are progressively smaller.

*Form.*—The florets are very round and unusually broad. They are wide open, ruffled and somewhat recurved and needle-pointed.

*Keeping qualities.*—Keeps and opens well.

Petals:

*Shape.*—Petals are broad, ruffled, recurved, round and needle-pointed.

*Size.*—The outer petals are 1¾ to 2½ inches in diameter and the inner petals are 1½ to 2 inches in diameter.

*Aspect.*—Substance is heavy; surface is smooth and ruffled at edges.

*Fragrance.*—None.

*Color.*—The largest area is light Gentian Blue 42/3, the edges of the petals being somewhat more intense. The blotch is Loeblia Blue 41/2.

Reproductive organs:

*Stamens.*—Large, very light cream with a hairline of violet which disappears as the stamen opens.

*Pistils.*—Three-pronged, extending about the same distance as the stamen; cream-colored.

*Comparisons*

My new variety resembles Libretto (unpatented) more than any other known variety, but differs from it principally as follows:

(1) My variety is taller and more rugged than Libretto.

(2) My variety has better substance than Libretto.

(3) My variety is larger, rounder and more formal than Libretto.

(4) My variety is more ruffled and more distinctive than Libretto.

(5) My variety has more consistent performance than Libretto.

(6) My variety has greater third dimension than Libretto.

(7) My variety opens more than does Libretto.

(8) My variety is healthier and a better propagator than Libretto.

Having thus disclosed my invention, I claim:

The new and distinct variety of gladiolus plant, substantially as herein shown and described, characterized by its consistent growth, size, health, beautifully ruffled florets, formal spike and improved color.

No references cited.